United States Patent [19]

Wright

[11] Patent Number: 4,867,265

[45] Date of Patent: Sep. 19, 1989

[54] PRE-CORDIAL STETHOSCOPE COVER

[76] Inventor: L. Bradley Wright, 8217 N. Overland Dr., Kansas City, Mo. 64151

[21] Appl. No.: 293,090

[22] Filed: Jan. 3, 1989

[51] Int. Cl.$^4$ .............................................. A61B 7/02
[52] U.S. Cl. .................................. 181/131; 181/137; 381/189
[58] Field of Search ................. 181/131, 137; 381/189

[56] References Cited

U.S. PATENT DOCUMENTS

| | | | |
|---|---|---|---|
| 2,115,478 | 4/1938 | Von Baussen | 181/131 X |
| 2,651,380 | 9/1953 | Brandenburg | 181/137 |
| 4,401,125 | 8/1983 | Taylor et al. | 181/171 X |

Primary Examiner—B. R. Fuller
Attorney, Agent, or Firm—Kokjer, Kircher, Bradley, Wharton, Bowman & Johnson

[57] ABSTRACT

A cover for a pre-cordial stethoscope provides protection for the stethoscope and reduces external noise contamination. The cover fits closely on the stethoscope body and includes a slot for receiving a tubular fitting which extends from the stethoscope body to transmit the monitored sounds. A shell presenting an internal vacuum chamber may be interposed between the cover and stethoscope body for enhanced noise suppression. Different embodiments of the cover are provided for adult and infant pre-cordial stethoscopes.

13 Claims, 1 Drawing Sheet

PRE-CORDIAL STETHOSCOPE COVER

BACKGROUND AND SUMMARY OF THE INVENTION

This invention relates in general to stethoscopes and more particularly to a protective cover for a pre-cordial stethoscope.

Pre-cordial stethoscopes are used for monitoring heart and lung sounds. The pre-cordial stethoscopes that are used for adults and children are generally cylindrical and have an open bottom cavity from which a tubular fitting extends for transmission of the bodily sounds that are detected. The pre-cordial stethoscopes used for infants and premature infants are somewhat smaller and have a discoidal shape. The sounds that are being monitored are subject to external noise contamination which can be a significant problem. Handling and protection of the stethoscope also present problems.

The present invention is directed to a cover for a pre-cordial stethoscope which serves to protect the stethoscope body, make it easier to handle, and decrease the external noise contamination. In accordance with the invention, a protective cover constructed of a relatively soft material includes a discoidal top which spans the stethoscope body and a cylindrical side wall which encircles the stethoscope body. The side wall has a slot through which the tubular fitting of the stethoscope extends. The cover is applied to the stethoscope body and leaves the monitoring cavity open at the bottom so that its ability to detect heart and lung sounds is not impaired.

A rigid disk may be secured to or incorporated in the top of the cover to provide stiffening. Another option is the incorporation of a vacuum filled shell in combination with the cover to provide additional suppression of external noise. A modified cover is provided for the smaller stethoscopes that are used for infants and premature infants.

DESCRIPTION OF THE DRAWING

In the accompanying drawing which forms a part of the specification and is to be read in conjunction therewith and in which like reference numerals are used to indicate like parts in the various views.

DETAILED DESCRIPTION OF THE INVENTION

Figure 1:
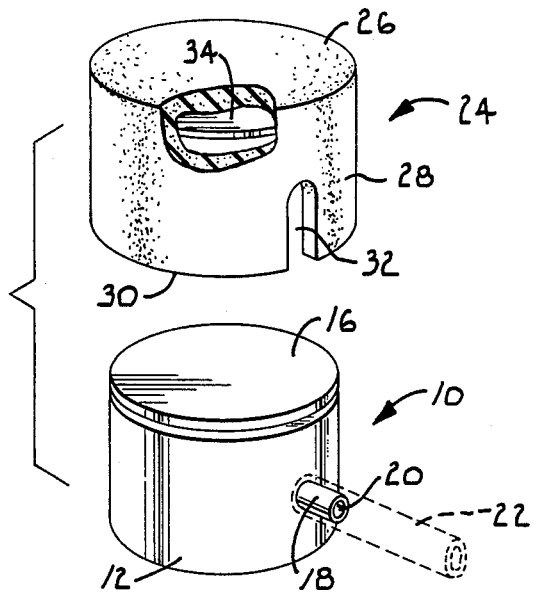
FIG. 1 is an exploded perspective view of a pre-cordial stethoscope and a cover constructed according to one embodiment of the present invention, with a portion of the cover broken away for purposes of illustration.
Figure 2:
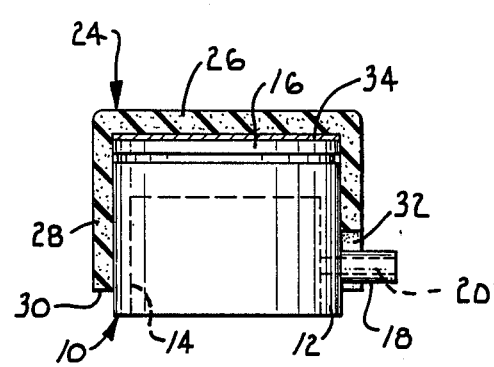
FIG. 2 is a sectional view showing the cover of FIG. 1 applied to the stethoscope.

Referring now to the drawing in more detail and initially to FIGS. 1 and 2, numeral 10 generally designates a pre-cordial stethoscope of the type commonly used to monitor the hearts and lungs of adults and children. The stethoscope 10 has a cylindrical body 12 which presents a cavity 14 (see FIG. 2) that is open at the bottom of the stethoscope body. The cavity 14 has a cylindrical shape and is closed at the top 16 of the stethoscope body. A tubular fitting 18 extends from the side of the stethoscope body 12 and has an internal passage 20 that extends from the cavity 14. A flexible tube 22 (FIG. 1) having ear pieces (not shown) on its ends may be connected with the fitting 18 in order to transmit the heart and lung sounds to the ear pieces.

In accordance with the present invention, the stethoscope 10 is fitted with a protective cover which is generally identified by reference numeral 24. The cover 24 includes a discoidal top 26 having a circular outer edge from which a cylindrical side wall 28 extends. The top 26 and side wall 28 of the cover are formed integrally from a relatively soft material such as rubber, soft plastic, rubberized plastic, or a similar material having good acoustical suppression properties as well as the necessary strength and texture.

The cylindrical side wall 28 of cover 24 has a circular lower edge 30. A slot 32 is formed in the side wall 28 and extends upwardly from the lower edge 30, terminating well below the top 26.

In order to provide rigidity to the cover 24 and particularly the top 26, a rigid disk 34 may be secured to or incorporated in the top 26. As best shown in FIG. 2, the disk 34 has substantially the same size as the top 26 and may be bonded or otherwise suitably secured to the underside of the top 26 at a location within the cover.

In use, the cover 24 may be applied to the stethoscope body 12 in the manner shown in FIG. 2. The top 26 spans the top of the stethoscope body, and the side wall 28 closely encircles the stethoscope body with the lower edge 30 located slightly above the bottom of the stethoscope body. The bottom of the cavity 14 remains open so that this side of the stethoscope body can be applied to the chest area of a patient in order to monitor heart and lung sounds.

The slot 32 is large enough and is located such that the tubular fitting 18 extends through it. Slot 32 is also preferably wide enough to accommodate the tube 22 so that the stethoscope is not hampered in its ability to transmit the sounds that are being monitored. If desired, the cover 24 may be secured to the stethoscope body by a suitable adhesive or in any other suitable manner.

Since the cover 24 substantially encloses the stethoscope body 12, the cover is able to effectively block external noise contamination and prevent it from reaching the monitoring cavity 14. At the same time, the relatively soft material of which the cover is constructed permits it to be handled more easily, and the cover also provides protection to the stethoscope body and prevents it from being damaged by externally applied forces.

Figure 3:
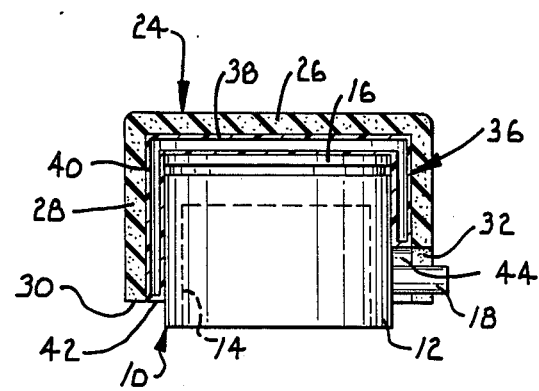
FIG. 3 is a sectional view showing a cover and a vacuum filled shell applied to a pre-cordial stethoscope in accordance with another embodiment of the invention.

FIG. 3 shows a modified form of the invention in which a hollow shell 36 is interposed between the cover 24 and the stethoscope body 12. The shell 36 has a generally discoidal top portion 38 which terminates in a circular outer edge from which a cylindrical side wall 40 extends. The side wall 40 is closed at its lower edge 42 and is provided with a slot 44 which extends upwardly from the lower edge 42. Within the top 38 and side wall 40 of shell 36, a vacuum chamber 48 is provided. The vacuum chamber 48 is evacuated and maintained under vacuum.

The cover 24 is large enough to closely receive shell 36 within it in the manner shown in FIG. 3. Similarly, the shell 36 has a size to closely fit on and around the stethoscope body 12. When the cover 24 and shell 36 are applied to one another and to the stethoscope body 12, the two slots 32 and 44 are in registration and the tubular fitting 18 extends through the mating slots 32 and 44.

The cover shown in FIG. 3 is somewhat larger than that shown in FIGS. 1 and 2 in order to accommodate the shell 36. In addition, the cover shown in FIG. 3 has no need for the stiffening disk 34. In all other respects, the cover 24 shown in FIG. 3 is identical to that shown in FIGS. 1 and 2, and it provides the same advantages described earlier. The shell 48 is applied to the stethoscope body 12 with its top portion 38 spanning the stethoscope body and its side wall 40 encircling the stethoscope body. Consequently, the stethoscope body is substantially surrounded by the vacuum within chamber 48 as well as by the cover 24, and this results in virtually eliminating the transmission of any external noise into the monitoring cavity 14.

Figure 4:
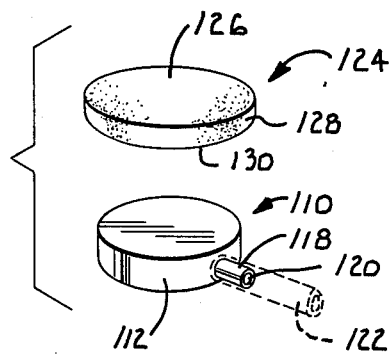
FIG. 4 is an exploded perspective view of a pre-cordial infant stethoscope and a cover therefor constructed in accordance with another embodiment of the invention.
Figure 5:
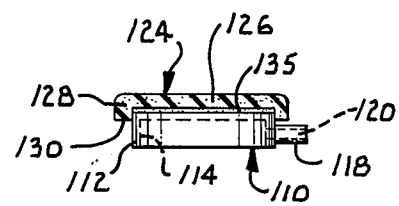
FIG. 5 is a sectional view showing the cover of FIG. 4 applied to the stethoscope.

Referring now to FIGS. 4 and 5, a modified form of the pre-cordial stethoscope cover is generally identified by numeral 124, and it is constructed particularly for application to a pre-cordial stethoscope 110 of the type used for infants and premature infants. The stethoscope 110 has a discoidal body 112 which presents an open bottom cavity 114 considerably smaller than the cavity 14 in the larger stethoscope body 12. A tubular fitting 118 projects from one side of the body 112 and has a passage 120 that extends from the cavity 114. A flexible tube 122 may be fitted on the fitting 118 in order to transmit the monitored sounds from the cavity 114 to ear pieces (not shown) carried on the distal end of the tube 122.

The cover 124 has a discoidal top 126 which presents a circular outer edge carrying a downturned annular lip 128. The top 126 and lip 128 are integral with one another and may be constructed of the same material as the cover 24. If desired, a stiffening disk similar to the disk 34 may be provided. The lip 128 has a circular lower edge 130.

In use, the cover 124 is applied to the stethoscope body 112 in a manner shown in FIG. 5. Adhesive 135 or some other suitable means may be employed to secure the cover 124 on the stethoscope body 112. When the cover is applied, the lower edge 130 is located slightly above the projecting tubular fitting 118 to avoid interfering with the fitting or the tube 122. As in the case of the other embodiments, the cover 124 serves to facilitate handling of the stethoscope body, to suppress external noise contamination and to provide protection for the stethoscope body. It is noted that the cover 124 completely covers the top of the stethoscope body 112 and enough of the side of the stethoscope body to successfully perform its noise suppressing function, since the noise in large part eminates from the area beyond the top of the stethoscope body.

It should be noted that the pre-cordial stethoscope may be milled or may otherwise be provided with a circumferential lip that the lower edge of the cover would abut. The cover is then essentially incorporated into the stethoscope.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A protective cover for a pre-cordial stethoscope having a cylindrical body presenting a cavity open at a bottom of a body and a tubular fitting on the body communicating with the cavity, said cover comprising:
   a discoidal top having a size to span the stethoscope body and having a circular outer edge;
   a generally cylindrical side wall extending from the edge of said discoidal top, said side wall terminating in a circular lower edge and being cooperable with said top to substantially cover the stethoscope body when applied thereto; and
   said top and wall being formed from a relatively soft material and the cavity in the stethoscope body remaining open at the bottom when the cover is applied to the stethoscope body.

2. The cover of claim 1, including a slot in said side wall extending from the lower edge thereof at a location to accommodate extension of the tubular fitting through said slot when the cover is applied to the stethoscope body.

3. The cover of claim 1, including a rigid disk secured to said discoidal top to stiffen same.

4. The cover of claim 3, including a slot in said side wall extending from the lower edge thereof at a location to accommodate extension of the tubular fitting through said slot when the cover is applied to the stethoscope body.

5. The cover of claim 1, including means for providing a vacuum chamber between the cover and the stethoscope body.

6. The cover of claim 1, including a hollow shell having a discoidal top between said discoidal top of the cover an the stethoscope body and a cylindrical side wall between the side wall of the cover and the stethoscope body, said shell presenting a vacuum chamber within the top and side wall thereof for suppressing noise.

7. The cover of claim 6, including mating slots in said side walls of the cover and shell at a location to accommodate extension of the tubular fitting through the slots when the cover and shell are applied to the stethoscope body.

8. In combination with a pre-cordial stethoscope having a cylindrical body presenting a cavity open at a bottom of the body and a tubular fitting projecting sidewardly from the body and communicating with the cavity, a protective cover comprising:
   a discoidal top spanning the stethoscope body and having a circular outer edge;
   a generally cylindrical side wall extending from said edge of the top and encircling the stethoscope body but leaving the cavity open at the bottom of the body, said side wall and top being formed integrally from a relatively soft material and said side wall terminating in a circular lower edge extending around the stethoscope body; and a slot in said side wall extending from the lower edge thereof at a location to receive the tubular fitting in extension through the slot.

9. The cover of claim 8, including a rigid disk secured to said discoidal top to stiffen same.

10. The cover of claim 8, including means for providing a vacuum chamber between the cover and the stethoscope body.

11. The cover of claim 8, including a hollow shell having a discoidal top between said discoidal top of the cover and the stethoscope body and a cylindrical side wall between the side wall of the cover and the stethoscope body, said shell presenting a vacuum chamber within the top and side wall thereof for supporting noise.

12. The cover of claim 11, including a slot in the side wall of said shell at a location to register with the slot in the side wall of the cover and to receive the tubular fitting in extension through both slots.

13. A protective cover for a pre-cordial infant stethoscope having a discoidal body with an open bottomed cavity therein and a laterally projecting tubular fitting communicating with the cavity, said cover comprising:

a discoidal top having a size to span the stethoscope body and having a circular outer edge;

an annular lip on the outer edge of said discoidal top projecting in a direction to encircle the stethoscope body when applied thereto, said top and lip being formed integrally from a relatively soft material and said lip terminating in an edge located above the tubular fitting to prevent the cover from interfering with the fitting; and means for adhesively securing said top to the stethoscope body.

* * * * *